US00PP29993P2

(12) United States Plant Patent
Korlipara

(10) Patent No.: US PP29,993 P2
(45) Date of Patent: Dec. 18, 2018

(54) ***LEUCANTHEMUM* PLANT NAMED 'COCONUT'**

(50) Latin Name: ***Leucanthemum* x *superbum***
Varietal Denomination: Coconut

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/732,364

(22) Filed: Oct. 31, 2017

(51) Int. Cl.
*A01H 5/02* (2018.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Klarquist Sparkman, LLP

(57) ABSTRACT

A new and distinct *Leucanthemum* plant named 'Coconut' characterized by double daisy type inflorescences, light yellow flower buds and young ray florets, numerous white ray florets with frilly tips around a large gold disc, excellent bloom size, a compact, upright habit, and excellent vigor.

1 Drawing Sheet

Botanical denomination: *Leucanthemum* x *superbum*.
Variety designation: 'Coconut'.

BACKGROUND OF THE INVENTION

The present invention relates to a new and distinct cultivar of *Leucanthemum* and given the cultivar name 'Coconut'. *Leucanthemum* is in the family Asteraceae. This new cultivar originated from a controlled cross between unknown, unnamed, proprietary *Leucanthemum* x *superbum* seedlings. This was part of a controlled breeding program to obtain dwarf *Leucanthemum*. *Leucanthemum* 'Coconut' was selected for its white double daisy inflorescences and its mounding, compact habit and upright stems.

Compared to *Leucanthemum* x *superbum* 'Belgian Lace', U.S. Plant Pat. No. 27,038, the new cultivar is later blooming and more upright.

This new *Leucanthemum* cultivar is distinguished as unique with its:

1. double daisy type inflorescences,
2. light yellow flower buds and young ray florets,
3. numerous white ray florets with frilly tips around a large gold disc,
4. excellent bloom size,
5. a compact, upright habit, and
6. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a single, 1 year old plant of the new cultivar growing in full sun in the trial field in early July in Canby, Oreg.

FIG. 2 shows a bank of 2 year old plants in Canby, Oreg.

DETAILED PLANT DESCRIPTION

The following is a detailed description of the new *Leucanthemum* cultivar based on observations of 1-year-old specimens growing in the garden in sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart, 5th* edition, 2007.

Plant:

*Type*.—Herbaceous perennial.
*Hardiness*.—USDA Zones 5 to 9.
*Size*.—39 cm wide and 31 cm tall to top of inflorescences.
*Form*.—Basal clump.
*Number of crowns*.—10.
*Vigor*.—Excellent.

Stem (flowering):

*Type*.—Ascending.
*Strength*.—Excellent, very strongly upright.
*Number of stems*.—About 10 stems from the crown, each flowering with 1 to 9 inflorescences.
*Size*.—Grows to about 25 to 30 cm tall to a terminal inflorescence and 8 mm wide at base.
*Internode length*.—1 to 3 cm.
*Surface texture*.—Pubescent.
*Color*.—Green 137A.

Leaf:

*Type*.—Simple.

*Shape*.—Lanceolate.

*Arrangement*.—Alternate.

*Blade size*.—Grows to 10 cm long and 30 mm wide.

*Margins*.—Coarsely serrate.

*Apex*.—Acute.

*Base*.—Clasping.

*Petiole*.—Sessile.

*Surface texture*.—Pubescent on both sides.

*Venation*.—Pinnate.

*Color*.—Topside Green 137B with main vein Yellow Green 147C, bottom side Yellow Green 147B with main vein Yellow Green 147C.

Inflorescence:

*Type*.—Composite on terminal stalked heads.

*Number of inflorescences per plant*.—About 47.

*Size*.—Grows to 8 cm wide and 4 cm deep.

*Form*.—Ray florets held upright when young, lower ray florets reflex down with maturity, mature disc is mostly flat.

*Bud* (*immature inflorescence from a lateral bud*).—20 mm wide and 15 mm deep, ray florets held vertically and cupped inwards, Yellow 6C.

*Ray florets*.—With 1 pistil and no stamen, about 120 in number, 100 normal size and 20 of reduced size near the disc florets, normal ray florets linear to oblong, tip with 2 to 4 lobes to 1 to 3 deeply parted segments, margins entire, base attenuate, grows to 30 mm long and 2 to 20 mm wide (20 mm with 3 segments), reduced ray florets linear or 2 to 3-laciniate segments cut to the base, usually 12 mm long and 3.5 mm wide, tip acute, margins entire, base attenuate, both sizes glabrous and Yellow 13D when young maturing to White NN155D on both sides; pistil 5 mm long, ovary 1.5 mm long, Yellow Green 149D, style 2.5 mm long, White 155A, 2-branched stigma 0.5 mm long, Yellow 13B.

*Disc*.—Slightly concave becoming convex, becoming 12 mm deep and 25 mm wide with maturity, Yellow Orange 15A.

*Disc florets*.—About 400 in number, each 6 mm long and 1.5 mm wide; corolla tubular, 4 mm long and 1.5 mm wide, 5 lobed, inside and out glabrous and Yellow 15A on top ½ and Yellow Green 145C on bottom ½; pistil 1, 5.5 mm long, ovary 2 mm long and Yellow Green 145D, style 2 mm long, Greyed Orange 163B, 2 branched stigma 1 mm long, Greyed Orange 163B; stamen 5 in number, 4 mm long, filaments 2 mm long, Greyed Orange 163B, anthers 2 mm, Greyed Orange N163B, pollen Yellow Orange 21D.

*Involucral bracts*.—In 3 imbricate whorls, area to 3 cm wide and 10 mm deep, lobes lanceolate in shape, grow to 7 mm long and 3 mm wide, Yellow Green 147B with margin membranous and Brown 200B, tip acute to piliferous, pubescent on back side and glabrous on inside.

*Receptacle*.—Grows to 22 mm wide and 5 mm deep, Yellow Green 145C.

*Bloom period*.—July through August in Canby, Oreg.

*Fragrance*.—None.

*Lastingness*.—Each inflorescence lasts about two weeks in Canby, Oreg.

Seeds: Few, each 3 mm long and 2 mm wide, oval, Brown 200C.

*Fertility*.—Poor.

Disease and pests: No problems have been found in Canby, Oreg. in the last 4 years. No known resistances to pests or diseases.

I claim:

1. A new and distinct *Leucanthemum* plant as herein illustrated and described.

* * * * *

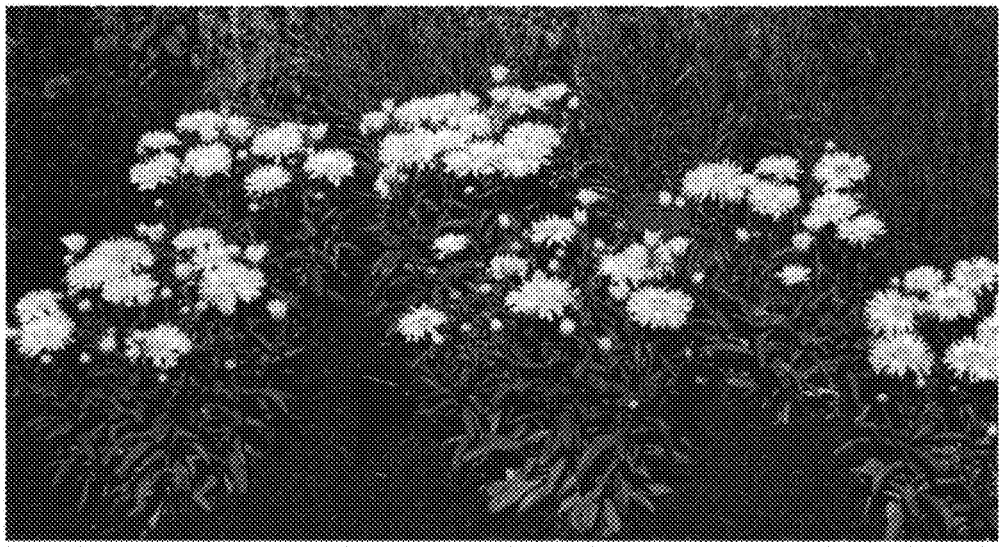

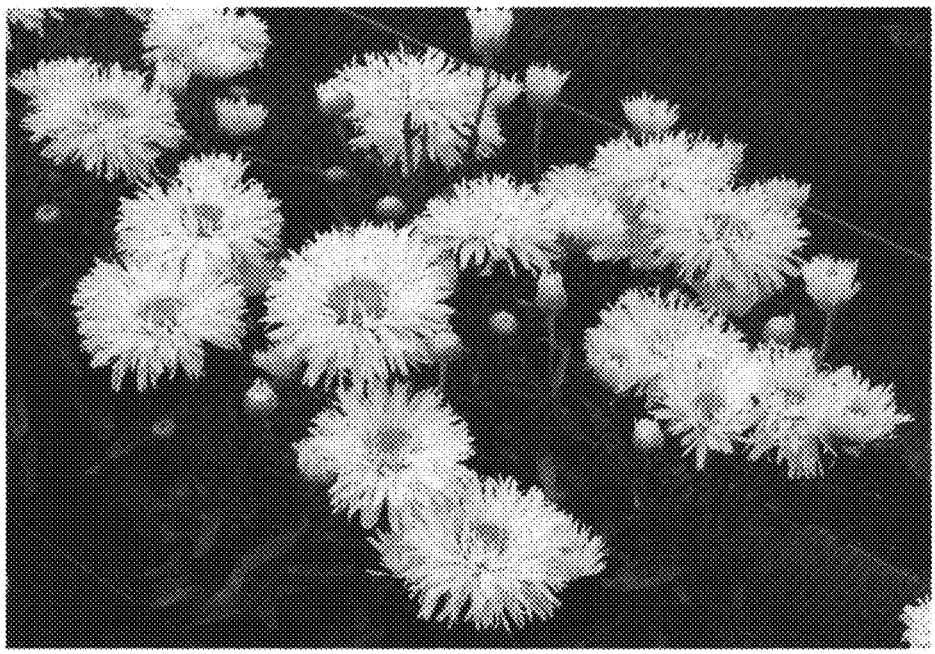
FIG. 1 above, FIG. 2 below